US010357451B2

(12) United States Patent
Nakauma et al.

(10) Patent No.: US 10,357,451 B2
(45) Date of Patent: Jul. 23, 2019

(54) ENTERAL NUTRITION

(71) Applicant: SAN-EI GEN F.F.I., INC., Toyonaka-shi, Osaka (JP)

(72) Inventors: Makoto Nakauma, Toyonaka (JP); Sayaka Ishihara, Toyonaka (JP); Satomi Nakao, Toyonaka (JP)

(73) Assignee: SAN-EI GEN F.F.I., INC., Toyonaka-shi, Osaka (JP)

( * ) Notice: Subject to any disclaimer, the term of this patent is extended or adjusted under 35 U.S.C. 154(b) by 0 days.

(21) Appl. No.: 14/440,938

(22) PCT Filed: Nov. 8, 2013

(86) PCT No.: PCT/JP2013/080357
§ 371 (c)(1),
(2) Date: Jun. 8, 2015

(87) PCT Pub. No.: WO2014/073675
PCT Pub. Date: May 15, 2014

(65) Prior Publication Data
US 2015/0290123 A1 Oct. 15, 2015

(30) Foreign Application Priority Data

Nov. 8, 2012 (JP) ................................. 2012-246087

(51) Int. Cl.
| | |
|---|---|
| *A23L 33/165* | (2016.01) |
| *A61K 9/00* | (2006.01) |
| *A61K 47/12* | (2006.01) |
| *A61K 47/36* | (2006.01) |
| *A23L 29/256* | (2016.01) |
| *A23L 33/00* | (2016.01) |

(52) U.S. Cl.
CPC .......... *A61K 9/0029* (2013.01); *A23L 29/256* (2016.08); *A23L 33/165* (2016.08); *A23L 33/40* (2016.08); *A61K 47/12* (2013.01); *A61K 47/36* (2013.01); *A23V 2002/00* (2013.01); *A23V 2200/00* (2013.01)

(58) Field of Classification Search
None
See application file for complete search history.

(56) References Cited

U.S. PATENT DOCUMENTS

| | | | | | |
|---|---|---|---|---|---|
| 4,744,986 | A | * | 5/1988 | Luber | .................... A61K 33/08 424/686 |
| 2005/0202079 | A1 | * | 9/2005 | Bielski | ................... A61K 9/205 424/451 |
| 2010/0256090 | A1 | * | 10/2010 | Yu | ........................... A23D 9/00 514/54 |

FOREIGN PATENT DOCUMENTS

| | | |
|---|---|---|
| EP | 2514321 A1 | 10/2012 |
| JP | 03-500170 A | 1/1991 |
| JP | 2009-291175 A | 12/2009 |
| JP | 2010-254598 A | 11/2010 |
| WO | 89/001790 A1 | 3/1989 |
| WO | WO 2011152706 A1 * | 12/2011 ........... A23L 1/0522 |
| WO | WO 2011152726 A1 * | 12/2011 ........... A23L 1/0522 |

OTHER PUBLICATIONS

Takahiro Funami et al. Food Hydrocolloids (2009), 23(7), 1746-1755.*
Shozo Miyazaki, "Development of food additives with in situ gelling properties of ionic responsible intelligent polysaccharides", The Japan Food Chemical Research Foundation, 2004, No. 10, pp. 104-108.
Sakie Noda, et al. "Influence of the mannuronate/guluronate ratio on the gelation of sodium alginate solutions in the presence of calcium", Dai 55 Kai Rheorogy Toronkai Koen Yoshishu, 2007, pp. 198-199.
International Search Report for PCT/JP2013/080357 dated Jan. 21, 2014 [PCT/ISA/210].
Communication dated Jun. 20, 2016, from the European Patent Office in counterpart European application No. 13853360.9.
Itoh et al., "In situ gelling xyloglucan/alginate liquid formulation for oral sustained drug delivery to dysphagic patients," Drug Development and Industrial Pharmacy, 2010, vol. 36, pp. 449-455.
Goh et al., "Alginates as a useful natural polymer for microencapsulation and therapeutic applications," Carbohydrate Polymers, vol. 88, 2012, pp. 1-12.
Patel et al., "Floating In Situ Gel based on Alginate as Carrier for Stomach-Specific Drug Delivery of Famotidine," International Journal of Pharmaceutical Sciences and Nanotechnology, vol. 3, Issue 3, 2010, pp. 1092-1104.

* cited by examiner

*Primary Examiner* — Nyeemah A Grazier
(74) *Attorney, Agent, or Firm* — Sughrue Mion, PLLC

(57) ABSTRACT

An object of the present invention is to provide an enteral nutrition that is simply injected and suppresses gastroesophageal reflux.
The present invention provides an enteral nutrition comprising 0.1 to 1.0 mass % of alginic acid and/or sodium salt thereof, calcium, and 0.1 to 3.5 parts by mass of a chelating agent per part by mass of the calcium.

7 Claims, No Drawings

ENTERAL NUTRITION

CROSS REFERENCE TO RELATED APPLICATIONS

This application is a National Stage of International Application No. PCT/JP2013/080357, filed on Nov. 8, 2013, which claims priority from Japanese Patent Application No. 2012-246087, filed on Nov. 8, 2012, the contents of all of which are incorporated herein by reference in their entirety.

TECHNICAL FIELD

The present invention relates to an enteral nutrition.

BACKGROUND ART

Nasogastric or oral tube feeding, and gastrostomy or jejunostomy tube feeding, have been conventionally used for the patients and the elderly who have difficulty taking food by mouth. Nasogastric or oral tube feeding is a method of continuously injecting nutrients such as liquid food via a tube inserted from the nose or mouth into the esophagus, stomach, duodenum, or jejunum; and gastrostomy or jejunostomy tube feeding is a method of continuously injecting nutrients such as liquid food via a tube placed in an external fistula that is surgically or endoscopically created at the esophagus or jejunum (often the stomach).

Since patients and the elderly to whom tube feeding is applied often have remarkably low function of the cardia at the upper stomach, gastro-esophageal reflux may occur when a liquid diet in the stomach is in the state of a low-viscosity liquid. To prevent gastro-esophageal reflux, the patient receiving the liquid diet must remain in the same seating position for a long period of time, and this imposes a great burden on care workers and the care recipient.

In contrast, when the liquid diet is in the state of a gel, or a high-viscosity liquid or paste, gastro-esophageal reflux can be suppressed. However, to inject the liquid diet through a tube, a high pressure must be applied for a long period of time, which also imposes a great burden on care workers.

To solve the above problems, Patent Literature 1 discloses a method for reducing or preventing vomiting, comprising tubal injection of a solution containing one or two or more members selected from kappa carrageenan, iota carrageenan, sodium alginate, and alginic acid before or after tubal injection of a mixture obtained by mixing a calcium ion supplier with an enteral nutrient.

CITATION LIST

Patent Literature

PTL 1: JP2010-254598A

SUMMARY OF INVENTION

Technical Problem

However, in the technique disclosed in Patent Literature 1, although it is not necessary to continuously apply pressure during injection, two liquids must be sequentially injected via a tube, which makes the injection complicated.

Accordingly, an object of the present invention is to provide an enteral nutrition that is simply injected and is not likely to cause gastro-esophageal reflux.

Solution to Problem

The present inventors conducted extensive research to achieve the object of providing an enteral nutrition that is simply injected and is not likely to cause gastro-esophageal reflux. As a result, they found that this object can be achieved if it is possible to form an enteral nutrition that is in the state of a high-fluidity and low-viscosity liquid when injected, but that becomes thickened or gelated in the stomach after injection (when the enteral nutrition comes into contact with gastric juice).

Research was conducted to provide such an enteral nutrition, and consequently, the inventors found that an enteral nutrition comprising 0.1 to 1.0 mass % of alginic acid and/or sodium salt thereof, calcium, and 0.1 to 3.5 parts by mass of a chelating agent per part by mass of the calcium is in the state of a high-fluidity and low-viscosity liquid when injected, but becomes thickened or gelated in stomach environments with a pH of 2.0 or less. Thus, the inventors found that the object described above can be achieved, and the invention was thus accomplished.

Specifically, the present invention includes the following embodiments.

Item 1. An enteral nutrition comprising 0.1 to 1.0 mass % of alginic acid and/or sodium salt thereof, calcium, and 0.1 to 3.5 parts by mass of a chelating agent per part by mass of the calcium.

Item 2. The enteral nutrition according to Item 1, wherein tube fluidity measured by the tube fluidity measurement method described below is 400 ml/hour or more.

Tube Fluidity Measurement Method 80 ml of a sample is placed in a 100-ml plastic bottle with an opening at an upper portion.

A flexible silicone tube with an inner diameter of 4 mm and a length of 1,000 mm is connected to the bottom of the plastic bottle.

The bottom surface of the plastic bottle is placed 600 mm above the end of the tube so that the sample flows out only by gravity via the tube.

The flow A (ml) of the sample that flows out in 10 minutes is measured with a measuring cylinder, and A×6 (ml/hour) is determined to be the tube fluidity of the enteral nutrition.

Item 3. The enteral nutrition according to Item 1 or 2, wherein the viscosity after injection to simulated gastric fluid, which is measured according to the measurement method of the viscosity after injection to simulated gastric fluid described below is 1,500 mPa·s or more.

Measurement Method of Viscosity after Injection to Artificial Gastric Juice 80 ml of a sample is placed in a 100-ml plastic bottle with an opening at an upper portion.

A flexible silicone tube with an inner diameter of 4 mm and a length of 1,000 mm and a speed regulator are connected to the bottom of the plastic bottle.

The flow speed is adjusted to 300 ml/hour with the speed regulator, and the total amount of the sample is directly added dropwise, via the tube, to a 100-ml beaker containing 20 ml of simulated gastric fluid (an aqueous solution containing 0.7% hydrochloric acid and 0.2% salt, pH of 1.2) maintained at 37° C. in a constant-temperature water bath.

The viscosity of the mixture at $1.0\ \text{s}^{-1}$ is measured by using a fluid rheometer under the following viscosity measurement conditions.

Viscosity Measurement Conditions

Geometry: Cone-plate plunger with a diameter of 50 mm and a gap of 0.051 mm

Measurement temperature: 20° C.
Shear rate: 1.0 s$^{-1}$

Item 4. The enteral nutrition according to any one of Items 1 to 3, wherein the proportion of an alginic acid and/or a sodium salt thereof having a guluronic acid/mannuronic acid ratio (G/M ratio) of 1.5 or less is 40 to 95 mass % relative to the total amount of the alginic acid and/or sodium salt thereof.

Item 5. The enteral nutrition according to any one of Items 1 to 4, wherein the proportion of an alginic acid and/or a sodium salt thereof having a weight average molecular weight (Mw) of 2.0×10$^5$ g/mol or less is 30 mass % or more relative to the total amount of the alginic acid and/or sodium salt thereof.

Item 6. The enteral nutrition according to any one of Items 1 to 5, wherein the chelating agent is citrate.

Item 7. The enteral nutrition according to any one of Items 1 to 6, which further comprises a polysaccharide other than alginic acid and/or sodium salt thereof.

Item 8. The enteral nutrition according to any one of Items 1 to 7, wherein the enteral nutrition is injected according to nasogastric or oral tube feeding, or gastrostomy or jejunostomy tube feeding.

Advantageous Effects of Invention

The enteral nutrition of the present invention is in the state of high-fluidity and low-viscosity when injected, but becomes thickened or gelated in stomach environments with a pH of 2.0 or less.

Thus, the present invention can provide an enteral nutrition that is simply injected and suppresses gastro-esophageal reflux.

DESCRIPTION OF EMBODIMENTS

The enteral nutrition of the present invention comprises 0.1 to 1.0 mass % of alginic acid and/or sodium salt thereof, calcium, and 0.1 to 3.5 parts by mass of a chelating agent per part by mass of the calcium.

The "enteral nutrition" in the present invention includes not only enteral nutritions (foods) but also nutrients (pharmaceutical products).

1. Alginic Acid and/or Sodium Salt Thereof

The "alginic acid and/or sodium salt thereof" used in the present invention is a substance widely used as a thickener for food additives. Alginic acid is a linear acid polysaccharide comprising uronic acid and is a copolymer of α-L-guluronic acid (G) and β-D-mannuronic acid (M). In the present specification, the molar ratio of α-L-guluronic acid (G) to β-D-mannuronic acid (M) is sometimes referred to as the "G/M ratio."

Alginic acid and/or sodium salt thereof is commercially available. Examples of sodium alginate include SAN SUPPORT™ P-70, P-71, P-72, P-81, and P-82 (trade name; San-Ei Gen F.F.I., Inc.). Examples of alginic acid include SAN SUPPORT P-90 (trade name; San-Ei Gen F.F.I., Inc.).

In the present invention, alginic acids and/or sodium salts thereof having various G/M ratios can be used as alginic acid and/or sodium salt thereof.

The alginic acids and/or sodium salts thereof used in the present invention can be used singly or in a combination of two or more.

For example, the alginic acid and/or sodium salt thereof used in the present invention may be the combination of at least two alginic acids and/or sodium salts thereof having different G/M ratios.

The proportion of the alginic acid and/or sodium salt thereof having a G/M ratio of 0.5 to 1.5 relative to the total amount of the alginic acid and/or sodium salt thereof used in the present invention is preferably 40 to 95 mass %, more preferably 50 to 90 mass %, and even more preferably 60 to 80 mass %.

In the above proportion range, the enteral nutrition of the present invention tends to have a low viscosity when injected (i.e., before coming into contact with gastric juice) and have a high viscosity in the stomach (after coming into contact with gastric juice).

Thus, the phrase "when injected" in this specification indicates the time before coming into contact with gastric juice.

The phrase "in the stomach" in this specification indicates the time after coming into contact with gastric juice.

For example, the alginic acid and/or sodium salt thereof used in the present invention may be the combination of at least two alginic acids and/or sodium salts thereof having a different weight average molecular weight.

The proportion of the alginic acids and/or sodium salts thereof having a weight average molecular weight of 2.0×10$^5$ g/mol or less relative to the total amount of the alginic acid and/or sodium salt thereof is preferably 30 mass % or more, more preferably 30 to 95 mass %, even more preferably 40 to 90 mass %, and particularly preferably 50 to 85 mass %.

In the above proportion range, the enteral nutrition of the present invention tends to have a low viscosity when injected and have a high viscosity in the stomach.

In the present invention, the alginic acid and/or sodium salt thereof is preferably a mixture of alginic acid and sodium salt thereof.

The content of the alginic acid and/or sodium salt thereof in the enteral nutrition of the present invention is preferably 0.1 to 1.0 mass %, more preferably 0.15 to 0.8 mass %, and even more preferably 0.2 to 0.5 mass %.

In the present invention, the content of sodium alginate, expressed precisely, is the content of alginic acid. However, the content of sodium alginate can actually be used as an approximate content of the alginic acid.

A content too low may result in insufficient thickening or gelation of the thick liquid diet in the stomach, while a content too high may result in viscosity too high when the enteral nutrition is injected.

2. Calcium

The form of calcium used in the present invention is not particularly limited, and is, for example, a salt or an ion.

The enteral nutrition of the present invention actually comprises a supply source of calcium.

The supply source of calcium may be at least one member selected from the group consisting of calcium chloride, calcium sulfate, calcium citrate, calcium gluconate, calcinated (sea urchin shell, shell, bone, reef-building coral, lactic, egg shell) calcium, uncalcinated (shell, bone, coral, nacreous layer, egg shell) calcium, calcium carbonate, calcium lactate, calcium monohydrogen phosphate, calcium dihydrogen phosphate, calcium trihydrogen phosphate, calcium tetraacetic acid ethylenediamine, and hydrates thereof. Preferably, at least one member selected from the group consisting of calcium chloride, calcium sulfate, calcium citrate, calcium carbonate, calcium lactate, and calcium monohydrogen phosphate can be used.

The supply sources of calcium may be used singly or in a combination of two or more.

The calcium may be contained in the nutrients explained later.

The content of calcium in the enteral nutrition of the present invention can be suitably determined based on the recommended dietary allowance amount, adequate intake, dietary goal, or tolerable upper intake level described in the *Dietary Reference Intakes for Japanese* 2010.

However, a content too low may result in insufficient thickening or gelation of the enteral nutrition, while a content too high may result in viscosity too high when the enteral nutrition is injected.

The content of calcium in the enteral nutrition of the present invention is preferably 0.01 to 0.25 mass %, more preferably 0.02 to 0.20 mass %, and even more preferably 0.05 to 0.15 mass %.

In the enteral nutrition of the present invention, calcium is preferably contained in an amount of 0.05 to 1.0 parts by mass, more preferably 0.08 to 0.8 parts by mass, and even more preferably 0.1 to 0.5 parts by mass per part by mass of the alginic acid and/or sodium salt thereof.

A ratio too low may result in insufficient thickening or gelation of the enteral nutrition in the stomach, while a ratio too high may result in viscosity too high when the enteral nutrition is injected.

3. Chelating Agent

In the present invention, at least one member selected from the group consisting of phosphate, condensed phosphate, malate, succinate, tartarate, glutamate, ethylenediaminetetraacetate, gluconate, citric acid, citrate, phytic acid, and phytate can be used as a chelating agent.

More specifically, it is possible to use at least one member selected from the group consisting of sodium dihydrogen phosphate, disodium hydrogen phosphate, trisodium phosphate, potassium dihydrogen phosphate, dipotassium hydrogen phosphate, tripotassium phosphate, calcium dihydrogenphosphate, dicalcium hydrogen phosphate, tricalcium phosphate, trimagnesium phosphate, tetrasodium pyrophosphate, disodium dihydrogen pyrophosphate, tetrapotassium pyrophosphate, calcium dihydrogen pyrophosphate, sodium polyphosphate, potassium polyphosphate, sodium metaphosphate, potassium metaphosphate, sodium malate, monosodium succinate, disodium succinate, sodium tartrate, potassium bitartrate, sodium glutamate, potassium glutamate, calcium glutamate, magnesium glutamate, calcium disodium ethylenediaminetetraacetate, disodium ethylenediaminetetraacetate, sodium gluconate, potassium gluconate, calcium gluconate, iron gluconate, copper gluconate, trisodium citrate, tripottasium citrate, calcium citrate, iron citrate, and sodium ferric citrate. Of these, for example, citrate is preferable, and at least one member selected from the group consisting of trisodium citrate and tripottasium citrate is more preferable.

The enteral nutrition of the present invention preferably contains a chelating agent in an amount of 0.005 to 0.15 mass %, more preferably 0.01 to 0.1 mass %, and even more preferably 0.02 to 0.08 mass %.

A content too low may result in viscosity too high when the enteral nutrition is injected, while a content too high may result in insufficient thickening or gelation of the enteral nutrition, or generate an instable component (e.g., protein, lipid) in the enteral nutrition, sometimes causing agglomeration or precipitation.

The enteral nutrition of the present invention contains a chelating agent in an amount of 0.1 to 3.5 parts by mass, preferably 0.2 to 3.0 parts by mass, and more preferably 0.35 to 1.5 parts by mass per part by mass of calcium contained in the added calcium chloride (anhydrous).

A ratio too low may result in viscosity too high when the enteral nutrition is injected, while a ratio too high may result in insufficient thickening or gelation of the enteral nutrition in the stomach.

The enteral nutrition of the present invention preferably contains a chelating agent in an amount of 0.04 to 0.6 parts by mass, more preferably 0.05 to 0.5 parts by mass, and even more preferably 0.06 to 0.4 parts by mass per part by mass of alginic acid and/or salt thereof.

A content too low may result in viscosity too high when the enteral nutrition is injected, while a content too high may result in insufficient thickening or gelation of the enteral nutrition in the stomach.

4. Nutrient

The enteral nutrition of the present invention preferably contains at least one nutrient having a caloric value of 1 kcal/mL or more, which is selected from the group consisting of proteins, lipids, carbohydrates, minerals, vitamins, etc.

The proteins may be those conventionally used in food. Specific examples of the proteins include powdered skim milk, defatted soy milk powder, casein, whey protein, whole milk protein, soybean protein, wheat protein, and decomposed materials of these proteins. Milk proteins such as whey protein and whole milk protein often form calcium salt state. Such calcium can also serve as calcium that is essential for the enteral nutrition of the present invention.

The content of the protein of the present invention is preferably 0.5 to 20.0 mass %, and more preferably 1.0 to 15.0 mass %.

The lipids may be those generally used for food. Specific examples of the lipids include soybean oil, cottonseed oil, safflower oil, cone oil, rice oil, coconut oil, perilla oil, sesame oil, linseed oil, palm oil, rapeseed oil, and like plant oils; sardine oil, cod liver oil, and like fish oils; and long-chain-fatty-acid triglycerides (LCT), medium-chain-fatty-acid triglycerides (MCT), etc., as a source of essential fatty acids. Of these, for example, medium-chain-fatty-acid triglycerides (MCT) having 8 to 10 carbon atoms are preferable. The use of medium-chain-fatty-acid triglyceride (MCT) increases lipid adsorption.

The content of the lipid in the nutrient of the present invention is preferably 0.5 to 20.0 mass %, and more preferably 1.0 to 15.0 mass %.

The carbohydrates may be those generally used for food. Examples of the carbohydrates include general various sugars including monosaccharides such as glucose and fructose, and disaccharides such as maltose and sucrose; sugar alcohols such as xylitol, sorbitol, glycerin, and erythritol; polysaccharides such as dextrin and cyclodextrin; oligosaccharides such as fructooligosaccharide, galactosaccharide, and lactosucrose; etc. Of these, for example, dextrin is preferable because of its low taste impact.

The content of the carbohydrate in the enteral nutrition of the present invention is preferably 0.5 to 30.0 mass %, and more preferably 1.0 to 20.0 mass %.

Examples of minerals other than calcium include sodium, potassium, magnesium, iron, copper, zinc, etc. The mineral may be in the form of a salt that is used as a food additive.

The amount of mineral in the enteral nutrition of the present invention can be suitably determined based on the recommended dietary allowance amount, adequate intake, dietary goal, or tolerable upper intake level described in the *Dietary Reference Intakes for Japanese* 2010. The usual contents determined according to the above are described below. The content of sodium can be 6,000 to 20,000 mg/L. The content of potassium can be 2,000 to 3,500 mg/L. The content of magnesium can be 260 to 650 mg/L. The content of iron can be 10 to 40 mg/L. The content of copper can be 1.6 to 9 mg/L. The content of zinc can be 7 to 30 mg/L.

Examples of vitamins include vitamin A, vitamin B1, vitamin B2, vitamin B6, vitamin B12, vitamin C, vitamin D, vitamin E, vitamin K, niacin, biotin, pantothenic acid, folic acid, etc.

The amount of vitamin in the enteral nutrition of the present invention can be suitably determined based on the recommended dietary allowance amount, adequate intake, dietary goal, or tolerable upper intake level described in the *Dietary Reference Intakes for Japanese* 2010. The usual contents determined according to the above are described below. The content of vitamin A can be 0.54 to 1.5 mg/L. The content of vitamin B1 can be 0.8 to 1.0 mg/L. The content of vitamin B2 can be 1 to 100 mg/L. The content of vitamin B6 can be 1.0 to 1,000 mg/L. The content of vitamin B12 can be 2.4 to 100 mg/L. The content of vitamin C can be 100 to 1,000 mg/L. The content of vitamin D can be 0.0025 to 0.05 mg/L. The content of vitamin E can be 8 to 600 mg/L. The content of vitamin K can be 0.055 to 30 mg/L. The content of niacin can be 13 to 30 mg/L. The content of biotin can be 0.030 to 0.1 mg/L. The content of pantothenic acid can be 5 to 100 mg/L. The content of folic acid is 0.2 to 1.0 mg/L.

The enteral nutrition of the present invention may contain polysaccharides other than alginic acid and/or sodium salt thereof. Such a polysaccharide is preferably a soybean polysaccharide, iota carrageenan, etc., to decrease the viscosity when the enteral nutrition is injected (before coming into contact with gastric juice). Other preferable examples include deacylated gellan gum, low methoxyl pectin, kappa carrageenan, etc., to increase the viscosity in the stomach (after coming into contact with gastric juice). The methyl esterification (or "ME") degree of the low methoxyl pectin is 50% or less, preferably 0% or more to less than 40%, and more preferably 5% or more to less than 15%. The molecular weight of the low methoxyl pectin is preferably 250,000 g/mol or less, and more preferably 80,000 g/mol or less.

When the enteral nutrition of the present invention contains a polysaccharide other than the alginic acid and/or sodium salt thereof, the content ratio of the polysaccharide is 0.1 to 50.0 parts by mass, preferably 0.2 to 25.0 parts by mass, and more preferably 0.25 to 20.0 parts by mass per part by mass of the alginic acid and/or sodium salt.

The enteral nutrition of the present invention can further contain an additive etc. that is usually contained in an enteral nutrition, as long as the effect of the present invention is attained.

5. Tube Fluidity

The enteral nutrition of the present invention is in a liquid state and preferably has tube fluidity, which is measured according to the tube fluidity measurement method described later, of 400 to 5,000 ml/h, and more preferably 600 to 4,000 ml/h.

Tube Fluidity Measurement Method 80 ml of a sample is placed in a 100-ml plastic bottle with an opening at an upper portion.

A flexible silicone tube with an inner diameter of 4 mm and a length of 1,000 mm is connected to the bottom of the plastic bottle.

The bottom surface of the plastic bottle is placed 600 mm above the end of the tube so that the sample flows out only by gravity via the tube.

The flow A (ml) of the sample that flows out in 10 minutes is measured with a measuring cylinder, and A×6 (ml/hour) is determined to be the tube fluidity (tube flow rate) of the enteral nutrition.

The plastic bottle and flexible silicone tube used in the tube fluidity measurement are a plastic bottle and flexible silicone tube usually used for oral tube feeding.

The enteral nutrition of the present invention satisfying the preferable conditions above is easy to inject through a tube.

6. Viscosity before Injection to Artificial Gastric Juice

The viscosity before injection of the enteral nutrition of the present invention to simulated gastric fluid can be measured under the following measurement conditions by using an ARES LS-1 fluid rheometer (trade name; TA instruments) or a fluid rheometer that obtains the same measurement results as the ARES LS-1 fluid rheometer. The viscosity before injection to the simulated gastric fluid can be considered the same as the viscosity at the time of injection. The viscosity before injection to the simulated gastric fluid is preferably 0.1 to 200 mPa·s, and more preferably 1 to 100 mPa·s.

Viscosity Measurement Conditions

Fluid rheometer: ARES LS-1 (trade name; TA instrument) or fluid rheometer that can obtain the same measurement results as ARES LS-1

Geometry: Cone-plate plunger with a diameter of 50 mm and a gap of 0.051 mm

Measurement temperature: 20° C.

Shear rate: $1.0\ s^{-1}$

The enteral nutrition of the present invention satisfying the preferable conditions above is easy to inject through a tube.

7. Viscosity after Injection to Artificial Gastric Juice

The state of the enteral nutrition of the present invention in the stomach is inferred by injecting the enteral nutrition to the simulated gastric fluid. The enteral nutrition of the present invention after injection to simulated gastric fluid may be a gel, or a high-viscosity solution, dispersion, or paste. The viscosity of the enteral nutrition of the present invention after injection to simulated gastric fluid can be measured according to the measurement method of the viscosity after injection to the simulated gastric fluid described below. The viscosity measured according to the measurement method is preferably 1,500 to 20,000 mPa·s, and more preferably 2,000 to 10,000 mPa·s.

Viscosity Measurement Method after Injection to Artificial Gastric Juice 80 ml of a sample is placed in a 100-ml plastic bottle with an opening at an upper portion.

A flexible silicone tube with an inner diameter of 4 mm and a length of 1,000 mm and a speed regulator are connected to the bottom of the plastic bottle.

The flow speed is adjusted to 300 ml/hour with the speed regulator, and the total amount of the sample is directly added dropwise to a 100-ml beaker containing 20 ml of simulated gastric fluid (an aqueous solution containing 0.7% hydrochloric acid and 0.2% salt, pH of 1.2) maintained at 37° C. in a constant-temperature water bath.

The viscosity of the mixture at $1.0\ s^{-1}$ is measured by using a fluid rheometer under the following viscosity measurement conditions.

"Added dropwise" in the measurement method indicates that the enteral nutrition is injected to simulated gastric fluid from the end of the tube through air in the state in which the end of the tube is not in contact with the gastric juice.

The plastic bottle and the flexible silicone tube used in the viscosity measurement method are a plastic bottle and flexible silicone tube usually used for oral tube feeding.

Viscosity Measurement Conditions

The conditions are the same as the viscosity measurement conditions in section "6. Viscosity (Viscosity before Injection to Artificial Gastric Juice)."

The results suggest that the enteral nutrition of the present invention is sufficiently thickened or gelated in the stomach. That is, the enteral nutrition of the present invention that satisfies the preferable conditions above is considered to be unlikely to cause gastro-esophageal reflux.

8. pH

The pH of the enteral nutrition in the present invention is usually 4.0 to 9.0, preferably 4.5 to 8.5, and more preferably 5.0 to 8.0.

A pH too low may result in a high viscosity when the enteral nutrition is injected, while a pH too high may degrade the taste of the enteral nutrition.

The pH can be adjusted by using, if necessary, a pH adjuster of an organic acid and/or a salt thereof, a pH adjuster of an inorganic acid and/or a salt thereof, etc. Examples of the pH adjuster include organic acids such as phytic acid, citric acid, lactic acid, gluconic acid, adipic acid, tartaric acid, and malic acid, and salts thereof, sodium carbonate, sodium bicarbonate, sodium hydroxide, etc. Citrate, etc., that can act as a chelating agent can also serve as a chelating agent that is essential for the enteral nutrition of the present invention.

9. Production Method

The enteral nutrition of the present invention can be produced by mixing components by any method as long as the alginic acid and/or sodium salt thereof are not in contact with calcium in the absence of a chelating agent.

Specifically, for example, an aqueous solution or dispersion containing a nutrient (which may contain calcium), a calcium source, and a chelating agent is prepared, and alginic acid and/or sodium salt thereof is added thereto, and mixed, thus obtaining the enteral nutrition of the present invention.

The resulting enteral nutrition of the present invention can be sterilized, if necessary, by retort sterilization under the conditions of 105 to 121° C. for 5 to 60 minutes after filling the container.

10. Use

The enteral nutrition of the present invention can be injected as are conventional liquid diets, by nasogastric or oral tube feeding, or gastrostomy or jejunostomy tube feeding.

In particular, since the enteral nutrition of the present invention has a low viscosity when injected (before coming into contact with gastric juice) and high tube fluidity, it can be injected via a thin tube with a low pressure such as 100 Pa or less, or without pressure, i.e., injected only by gravity (injected by free drip). Thus, the enteral nutrition of the present invention can be injected by nasogastric or oral tube feeding, or gastrostomy or jejunostomy tube feeding, which are methods less stressful for the person being feed. The gastrostomy and intestinal fistula can be created, for example, by percutaneous endoscopic gastrostomy (PEG) and percutaneous endoscopic jejunostomy (PEJ), respectively.

Additionally, since the enteral nutrition of the present invention is thickened or gelated in the stomach (after coming into contact with gastric juice), gastro-esophageal reflux is not likely to occur, and the seating position of the person being feed does not need to remain the same for a long period of time.

EXAMPLES

Examples are given below to illustrate the present invention in more detail; however, the present invention is not limited to these Examples.

In the following, the superscript "TM" denotes a trademark name.

In the Examples of the present invention, SAN SUPPORT™ P-70, P-71, P-72, P-81, and P-82 (San-Ei Gen F.F.I., Inc.) were used as sodium alginate. SAN SUPPORT™ P-90 (San-Ei Gen F.F.I., Inc.) was used as alginic acid.

Table 1 shows the G/M ratios and weight average molecular weights ($M_w$; g/mol) of the alginic acid and sodium alginate measured by the methods described below.

In the following, sodium alginate having a G/M ratio of 1.5 or less is referred to as "sodium alginate with a low content of guluronic acid" (which may be abbreviated as "low GA"), whereas sodium alginate having a G/M ratio of 1.5 or more is referred to as "sodium alginate with a high content of guluronic acid" (which may be abbreviated as "high GA").

In addition, sodium alginate having a weight average molecular weight of less than $2.0 \times 10^5$ g/mol is referred to as "low-molecular-weight sodium alginate" (which may be abbreviated as "low MwA"), whereas sodium alginate having a weight average molecular weight of $2.0 \times 10^5$ g/mol or more is referred to as "high-molecular-weight sodium alginate" (which may be abbreviated as "high MwA").

(1) Method for Measuring G/M Ratio

The G/M ratios of sodium alginate and of alginic acid were determined by dividing the peak area from 5.00 to 5.15 ppm based on the proton bonded to the carbon at the 1-position of guluronic acid by the peak area from 4.60 to 4.75 ppm based on the proton bonded to the carbon at the 1-position of mannuronic acid. The peak areas were observed in measurement by1H-NMR.

The method for preparing samples and $^1$H-NMR measurement method are described below.

Sodium alginate and alginic acid samples were dissolved in deuterium oxide and then freeze-dried. This operation was repeated three times, and exchangeable protons were removed, followed by drying under reduced pressure for 24 hours. Each of the samples obtained by drying under reduced pressure was dissolved in deuterium oxide so as to have a content of about 2 mass %, and sodium trimethylsilylpropionate (TSP) was added as an internal standard. The $^1$H-NMR measurement was performed with an ECA600 NMR measurement apparatus (JEOL Ltd.) under the following conditions.

$^1$H-NMR Measurement Conditions

Magnetic field strength: 14.096 T
Frequency: 600 MHz
Pulse angle: 45°
Pulse time: 6.75 microseconds
Relaxation time: 5 seconds
Number of scans: 128
Measurement temperature: 70° C.

(2) Method for Measuring Weight Average Molecular Weight ($M_w$)

The weight average molecular weight ($M_w$) of sodium alginate was determined by separating a diluted sodium alginate solution by size separation chromatography and measuring the weight average molecular weight with a multiangle light scattering detector and a refractive index detector by the following method.

Method for Measuring Weight Average Molecular Weight ($M_w$)

1.5 g of sodium alginate on a dry weight basis was added to 100 g of ion-exchanged water, and the mixture was stirred with a Polytron homogenizer at a rotation speed of 26,000 rpm for 1 minute to disperse sodium alginate, thereby preparing a 1.5 weight % sodium alginate dispersion. The dispersion was diluted 30-fold with 0.5 M $NaNO_3$ aqueous solution and stirred with a Polytron homogenizer at a rotation speed of 26,000 rpm for 1 minute to prepare a 0.05 mass % sodium alginate dispersion. The obtained dispersion was filtered through a PTFE membrane filter with a pore size of 0.45 µm to remove insoluble matter, followed by gel permeation chromatography under the following conditions. The weight average molecular weight ($M_w$; g/mol) was then calculated using ASTRA Version 4.9 software (Wyatt Technology Corporation) from measurement values obtained by using a multiangle light scattering detector and a refractive index detector.

Gel Permeation Chromatography Measurement Conditions
Column: OHpak SB-806M HQ (Showa Denko)
Column temperature: 25° C.
Flow rate: 0.5 ml/min
Eluent: 0.5 M $NaNO_3$
Amount of sample liquid: 100 µl

TABLE 1

| | G/M ratio | $M_w$ (g/mol) | Classification |
|---|---|---|---|
| SAN SUPPORT ™ P-70 | 0.641 | $1.75 \times 10^5$ | Low GA, Low $M_wA$ |
| SAN SUPPORT ™ P-71 | 1.035 | $2.03 \times 10^5$ | Low GA, High $M_wA$ |
| SAN SUPPORT ™ P-72 | 1.348 | $2.92 \times 10^5$ | Low GA, High $M_wA$ |
| SAN SUPPORT ™ P-81 | 2.862 | $1.87 \times 10^5$ | High GA, Low $M_wA$ |
| SAN SUPPORT ™ P-82 | 2.991 | $2.37 \times 10^5$ | High GA, High $M_wA$ |

As a result of analysis, SAN SUPPORT™ P-70, P-71, and P-72 were classified as sodium alginate with a low content of guluronic acid (low GA), whereas SAN SUPPORT™ P-81 and P-82 were classified as sodium alginate with a high content of guluronic acid (high GA).

Further, SAN SUPPORT™ P-70 and SAN SUPPORT™ P-81 were classified as low-molecular-weight sodium alginate (low MwA), whereas SAN SUPPORT™ P-71, P-72, and P-82 were classified as high-molecular-weight sodium alginate (high MwA).

Experiment Example 1

Thick liquid diets were prepared using sodium alginate or another polysaccharide as described in (1-1) below, and each enteral nutrition was tested for viscosity before and after being injected to simulated gastric fluid and for tube fluidity before being injected to simulated gastric fluid as described in (1-2) below.

(1-1) Preparation of Thick Liquid Diets

First, a basic enteral nutrition having the composition shown in Table 2 was prepared. The basic enteral nutrition had a pH of 6.8.

Next, trisodium citrate was added to 80 g of the basic enteral nutrition so as to have the content described in Table 3, and the mixture was stirred and dissolved with a propeller stirrer at 500 rpm for 1 minute. Further, 20 g of an aqueous solution containing SAN SUPPORT™ P-70 and SAN SUPPORT™ P-81, which are sodium alginate, SAN ACE™, which is xanthan gum, or VIS TOP™ D-2029, which is guar gum (all from San-Ei Gen F.F.I., Inc.) in the individual amounts described in Table 3 was added. Each mixture was uniformly mixed by stirring with a propeller stirrer at 500 rpm for 10 minutes, thereby preparing the enteral nutritions of Examples 1 to 5 and Comparative Examples 1 to 5, each in an amount of 100 g.

TABLE 2

| | Content (g) |
|---|---|
| Casein Sodium | 3.44 |
| Isolated Soybean Protein | 0.52 |
| Corn Oil | 3.52 |
| Dextrin[1] | 9.40 |
| Purified Sucrose | 4.32 |
| HOMOGEN No. 897[2] | 0.10 |
| Magnesium Chloride (Anhydrous) | 0.16 |
| Pottasium Chloride (Anhydrous) | 0.12 |
| Calcium Chloride (Anhydrous) | 0.15 |
| Ion-exchanged Water | 58.27 |
| Total | 80.00 |

[1] DE value: 16.0 to 19.0 (San-Ei Gen F.F.I., Inc.)
[2] Emulsifier preparation (San-Ei Gen F.F.I., Inc.)
Glycerin fatty acid ester: 30 mass %
Sucrose fatty acid ester: 20 mass %
Glucose: 50 mass %

TABLE 3

| | Example 1 | Example 2 | Example 3 | Example 4 | Example 5 |
|---|---|---|---|---|---|
| Trisodium Citrate | 0.05 g | 0.02 g | 0.08 g | 0.05 g | 0.05 g |
| SAN SUPPORT ™ P-70 (Sodium Alginate) | 0.20 g | 0.20 g | 0.20 g | 0.10 g | 0.30 g |
| SAN SUPPORT ™ P-82 (Sodium Alginate) | 0.10 g | 0.10 g | 0.10 g | 0.05 g | 0.15 g |
| SAN ACE ™ (Xanthan Gum) | — | — | — | — | — |
| VIS TOP ™ D-2029 (Guar Gum) | — | — | — | — | — |
| Ion-exchanged Water | 19.65 g | 19.68 g | 19.62 g | 19.80 g | 19.50 g |
| Total of Above Components Plus Basic Thick Liquid Diet | 100 g | 100 g | 100 g | 100 g | 100 g |

TABLE 3-continued

| | Comparative Example 1 | Comparative Example 2 | Comparative Example 3 | Comparative Example 4 | Comparative Example 5 |
|---|---|---|---|---|---|
| Trisodium Citrate | — | 0.20 g | 0.05 g | 0.05 g | 0.05 g |
| SAN SUPPORT ™ P-70 (Sodium Alginate) | 0.20 g | 0.20 g | — | — | — |
| SAN SUPPORT ™ P-82 (Sodium Alginate) | 0.10 g | 0.10 g | — | — | — |
| SAN ACE ™ (Xanthan Gum) | — | — | — | 0.30 g | — |
| VIS TOP ™ D-2029 (Guar Gum) | — | — | — | — | 0.30 g |
| Ion-exchanged Water | 19.70 g | 19.5 g | 19.95 g | 19.65 g | 19.65 g |
| Total of Above Components Plus Basic Thick Liquid Diet | 100 g | 100 g | 100 g | 100 g | 100 g |

(1-2) Measurement Method
(1-2-1) Viscosity before Injection to Artificial Gastric Juice The viscosity at $1.0 \text{ s}^{-1}$ of each of the enteral nutritions prepared in (1-1) described above was measured with an ARES LS-1 fluid rheometer (trade name; produced by TA Instruments) under the following conditions.
Viscosity Measurement Conditions
Geometry: Cone-plate plunger with a diameter of 50 mm and a gap of 0.051 mm
Measurement temperature: 20° C.
Shear rate: $1.0 \text{ s}^{-1}$
(1-2-2) Viscosity after Injection to Artificial Gastric Juice 80 ml of each enteral nutrition was placed in a separate 100-ml plastic bottle with an opening at an upper portion, and a flexible silicone tube with an inner diameter of 4 mm and a length of 1,000 mm and a speed regulator were connected to the bottom of each plastic bottle. The total amount of each enteral nutrition was directly added dropwise via the tubes to a separate 100-ml beaker containing 20 ml of simulated gastric fluid (an aqueous solution containing 0.7% hydrochloric acid and 0.2% salt, pH of 1.2) maintained at 37° C. in a constant-temperature water bath (at which time, the end of each tube was placed 50 mm or more above the liquid surface of the simulated gastric fluid, and thus the end of each tube was not in contact with the simulated gastric fluid). The flow speed was adjusted to 300 ml/hour with the speed regulator.

The viscosity of each enteral nutrition at $1.0 \text{ s}^{-1}$ (in the following, "viscosity" denotes viscosity at $1.0 \text{ s}^{-1}$ unless otherwise specified) was measured with an ARES LS-1 fluid rheometer (produced by TA Instruments) under the conditions described in (1-2-1).
(1-2-3) Tube Fluidity 80 ml of each of the enteral nutritions prepared in (1-1) was placed in a separate 100-ml plastic bottle with an opening at an upper portion, and a flexible silicone tube with an inner diameter of 4 mm and a length of 1,000 mm was connected to the bottom of each plastic bottle. The bottom surface of each plastic bottle was placed 600 mm above the end of its tube so that the enteral nutrition flows out via the tube. When doing so, each enteral nutrition was allowed to flow out only by gravity via its tube. The flow A (ml) of each sample that flowed out in 10 minutes was measured with a measuring cylinder, and A×6 (ml/hour) was determined to be the tube fluidity of the enteral nutrition.
(1-3) Results Table 4 shows the viscosity before and after injection to simulated gastric fluid, ratio of viscosity after injection to viscosity before injection (increase in viscosity), and tube fluidity of each enteral nutrition.

TABLE 4

| | pH | Trisodium Citrate/ Calcium (Mass Ratio) | Viscosity before Injection (mPa·s) | Viscosity after Injection (mPa·s) | Increase in Viscosity (Times) | Tube Fluidity (ml/hour) |
|---|---|---|---|---|---|---|
| Ex. 1 | 6.5 | 0.93 | 89 | 2780 | 31.2 | 788 |
| Ex. 2 | 6.5 | 0.37 | 112 | 2850 | 17.5 | 685 |
| Ex. 3 | 6.7 | 1.48 | 95 | 2500 | 26.3 | 726 |
| Ex. 4 | 6.5 | 0.93 | 73 | 1865 | 28.7 | 1050 |
| Ex. 5 | 6.3 | 0.93 | 148 | 3845 | 26.0 | 485 |
| Comp. Ex. 1 | 6.2 | — | 548 | 1165 | 2.1 | —* |
| Comp. Ex. 2 | 6.8 | 3.70 | 277 | 2160 | 9.5 | 280 |
| Comp. Ex. 3 | 6.8 | 0.93 | 63 | 86 | 0.7 | 1150 |
| Comp. Ex. 4 | 6.5 | 0.93 | 637 | 446 | 0.7 | —* |
| Comp. Ex. 5 | 6.7 | 0.93 | 75 | 70 | 0.9 | 975 |

*Impossible to measure the speed.

In each of the enteral nutritions in Examples 1 to 5, the viscosity before injection to simulated gastric fluid was 200 mPa·s or less, and the tube fluidity was 400 ml/hour or more.

The enteral nutritions of Examples 1 to 5 each had a viscosity of 1,500 mPa·s or more after injection to simulated gastric fluid.

This result reveals that the enteral nutrition of the present invention has a low viscosity when injected into the stomach and is allowed to flow (flow out) only by gravity even when passed through a tube with an inner diameter of 4 mm, and that the enteral nutrition of the present invention in an amount of 200 to 400 ml, which is a standard amount injected at one time, can be injected in 30 to 60 minutes, or less.

Although an injection rate too high is problematic in that it tends to cause diarrhea or vomiting, the injection rate can be easily decreased by using a speed regulator or the like.

These results suggest that the enteral nutrition of the present invention reduces the burden on care workers and care recipients in injection into the stomach, and the viscosity of the enteral nutrition of the present invention is thought to become high enough in the stomach to prevent gastro-esophageal reflux.

In contrast, the viscosity of the enteral nutrition of Comparative Example 1, which does not contain trisodium citrate, which is a chelating agent, was so high that the enteral nutrition of Comparative Example 1 could not flow in the tube with an inner diameter of 4 mm only by gravity.

In the enteral nutrition of Comparative Example 2, which contains 0.2% trisodium citrate, precipitation of aggregates was observed before injection to simulated gastric fluid, and the tube fluidity was low.

In Comparative Example 3, which contains neither sodium alginate nor other polysaccharides, the viscosity after injection to simulated gastric fluid did not become high enough to prevent gastro-esophageal reflux.

In Comparative Examples 4 and 5, which contain xanthan gum or guar gum instead of sodium alginate, the viscosity after injection to simulated gastric fluid was lower than the viscosity before injection to simulated gastric fluid. In Comparative Example 4, the viscosity before injection to simulated gastric fluid was too high to exhibit sufficient tube fluidity. In Comparative Example 5, the viscosity after injection to simulated gastric fluid was unsatisfactory.

Experiment Example 2

Thick liquid diets were prepared using various types of sodium alginate having different G/M ratios and average molecular weights as described in (2-1) below, and each enteral nutrition was tested for viscosity before and after being injected to simulated gastric fluid and for tube fluidity before being injected to simulated gastric fluid as described in (2-2) below.

(2-1) Preparation of Enteral Nutritions 0.05 g of trisodium citrate was directly added to 80 g of a basic enteral nutrition having the composition shown in Table 2, and the mixture was stirred and dissolved with a propeller stirrer at 500 rpm for 1 minute. 20 g of an aqueous solution containing SAN SUPPORT™ P-70, P-71, P-72, P-81, or P-82, which are sodium alginate (all from San-Ei Gen F.F.I., Inc.) in the individual amounts described in Table 5 was separately prepared, added, and mixed. Each mixture was uniformly mixed by stirring with a propeller stirrer at 500 rpm for 10 minutes, thereby preparing the enteral nutritions of Examples 6 to 14. The trisodium citrate/calcium ratio (mass ratio) of each enteral nutrition was the same as that of the enteral nutrition in Example 1. Table 5 also shows the composition of the enteral nutrition in Example 1.

TABLE 5

| Sodium Alginate | | Example 1 | Example 6 | Example 7 | Example 8 | Example 9 |
|---|---|---|---|---|---|---|
| SAN SUPPORT™ P-70 | Low GA Low $M_w$A | 0.20 | 0.15 | 0.25 | — | — |
| SAN SUPPORT™ P-71 | Low GA High $M_w$A | — | — | — | 0.20 | 0.15 |
| SAN SUPPORT™ P-72 | Low GA High $M_w$A | — | — | — | — | — |
| SAN SUPPORT™ P-81 | High GA Low $M_w$A | — | — | — | 0.10 | 0.15 |
| SAN SUPPORT™ P-82 | High GA High $M_w$A | 0.10 | 0.15 | 0.05 | — | — |

| Sodium Alginate | | Example 10 | Example 11 | Example 12 | Example 13 | Example 14 |
|---|---|---|---|---|---|---|
| SAN SUPPORT™ P-70 | Low GA Low $M_w$A | — | 0.15 | — | — | 0.10 |
| SAN SUPPORT™ P-71 | Low GA High $M_w$A | 0.25 | 0.15 | — | 0.10 | — |
| SAN SUPPORT™ P-72 | Low GA High $M_w$A | — | — | — | — | 0.10 |
| SAN SUPPORT™ P-81 | High GA Low $M_w$A | 0.05 | — | 0.15 | 0.20 | — |
| SAN SUPPORT™ P-82 | High GA High $M_w$A | — | — | 0.15 | — | 0.10 |

(2-2) Measurement Method

The viscosity before injection to simulated gastric fluid, the viscosity after, and the tube fluidity before injection to simulated gastric fluid were measured for each of the thus-prepared enteral nutritions in the same manner as in (1-2) described above.

(2-3) Results

Table 6 shows the viscosity before and after injection to simulated gastric fluid, ratio of viscosity after injection to viscosity before injection (increase in viscosity), and tube fluidity of each enteral nutrition. For comparison, Table 6 shows the test results of the enteral nutrition of Example 1 in Experiment Example 1.

TABLE 6

| | Content of Low GA (wt %) | Content of Low $M_w$A (wt %) | Viscosity before Injection (mPa · s) | Viscosity after Injection (mPa · s) | Increase in Viscosity (Times) | Tube Fluidity (ml/hour) |
|---|---|---|---|---|---|---|
| Example 1 | 66.7 | 66.7 | 89 | 2780 | 31.2 | 788 |
| Example 6 | 50.0 | 50.0 | 98 | 2540 | 25.9 | 685 |
| Example 7 | 83.3 | 83.3 | 75 | 2250 | 30.0 | 975 |
| Example 8 | 66.7 | 33.3 | 115 | 2860 | 23.5 | 650 |

TABLE 6-continued

|  | Content of Low GA (wt %) | Content of Low $M_wA$ (wt %) | Viscosity before Injection (mPa·s) | Viscosity after Injection (mPa·s) | Increase in Viscosity (Times) | Tube Fluidity (ml/hour) |
|---|---|---|---|---|---|---|
| Example 9 | 50.0 | 50.0 | 110 | 2580 | 20.5 | 687 |
| Example 10 | 83.3 | 16.7 | 148 | 3250 | 21.1 | 511 |
| Example 11 | 100.0 | 50.0 | 110 | 1950 | 17.7 | 700 |
| Example 12 | 0.0 | 50.0 | 123 | 1700 | 13.8 | 555 |
| Example 13 | 33.3 | 66.7 | 195 | 2490 | 12.8 | 415 |
| Example 14 | 66.7 | 33.3 | 131 | 2950 | 22.5 | 533 |

In Example 1 and Examples 6 to 14, the viscosity before injection to simulated gastric fluid was 200 mPa·s or less, the viscosity after injection to simulated gastric fluid was 1,500 mPa·s or more, and the ratio of viscosity after injection to simulated gastric fluid to viscosity before was 10 or more.

In each Example, the tube fluidity was 400 ml/hour or more. Thus, the enteral nutrition of the present invention is considered to enable a care worker to help a care recipient easily take food.

Among the Examples, in Examples 1, 6 to 10, and 14, in which the content of low GA, i.e., the content of sodium alginate having a G/M ratio of 1.5 or less, is 50 mass % to 83.3 mass %, the viscosity after injection to simulated gastric fluid increased to 2,000 mPa·s or more, and the rate of increase in viscosity from before to after injection to simulated gastric fluid was as high as 20 times or more. These results clarify that increase in viscosity can be improved when low GA and high GA are contained in well-balanced proportions.

The results further clarify that when the content of low GA is the same, an enteral nutrition in which the content of low MwA, i.e., the content of sodium alginate having a weight average molecular weight of $2.0 \times 10^5$ g/mol or less, is 50.0 mass % or more tends to have a higher ratio of viscosity after injection to simulated gastric fluid to viscosity before, and that increase in viscosity can be improved when low MwA and high MwA are contained in well-balanced proportions.

Experiment Example 3

Thick liquid diets were prepared using sodium alginate and other polysaccharides in the individual combinations as described in (3-1) below, and each enteral nutrition was tested for viscosity before and after injection to simulated gastric fluid and for tube fluidity before injection to simulated gastric fluid as described in (3-2) below.

(3-1) Preparation of Thick Liquid Diets 0.05 g of trisodium citrate was added to 80 g of a basic enteral nutrition having the composition shown in Table 2, and the mixture was stirred and dissolved with a propeller stirrer at 500 rpm for 1 minute. Added was 20 g of an aqueous solution containing SAN SUPPORT™ P-70 and P-82, which are sodium alginate, and SAN SUPPORT™ P-90, which is alginic acid, Kelcogel™, which is deacylated gellan gum, SM-1200, which is a soybean polysaccharide, SAN SUPPORT™ P-120, P-130, P-140, P-150, P-160, or P-170, which are low methoxyl pectin, or SAN SUPPORT™ P-170, which is high methoxyl pectin (all from San-Ei Gen F.F.I., Inc.; Kelcogel is a trademark of CP Kelco). The amounts of the components are described in Tables 7 and 8. Each mixture was uniformly mixed by stirring with a propeller stirrer at 500 rpm for 10 minutes, thereby preparing the enteral nutritions of Examples 15 to 23. The trisodium citrate/calcium ratio (mass ratio) of each enteral nutrition was the same as that of the enteral nutrition of Example 1. Table 7 also shows the composition of the enteral nutrition of Example 1.

Note that the gellan gum was dissolved by heating at 85° C. for 15 minutes and used, and that the other polysaccharides were dissolved in ion-exchanged water at ordinary temperature and used.

TABLE 7

|  | Example 1 | Example 15 | Example 16 | Example 17 | Example 18 |
|---|---|---|---|---|---|
| Trisodium Citrate | 0.05 g | 0.05 g | 0.05 g | 0.05 g | 0.05 g |
| SAN SUPPORT ™ P-70 (Sodium Alginate) | 0.20 g | 0.20 g | 0.20 g | 0.20 g | 0.20 g |
| SAN SUPPORT ™ P-82 (Sodium Alginate) | 0.10 g | 0.10 g | 0.10 g | 0.10 g | 0.10 g |
| SAN SUPPORT ™ P-90 (Alginic Acid) | — | 0.20 g | — | — | — |
| Kelcogel ™ (Gellan Gum) | — | — | 0.20 g | — | — |
| SM-1200 (Soybean Polysaccharide) | — | — | — | 1.00 g | — |
| SAN SUPPORT ™ P-120 (Low Methoxyl Pectin) ME: 35.0% $M_w$: 125.4 kg/mol | — | — | — | — | 0.20 g |
| Ion-exchanged Water | 19.65 g | 19.45 g | 19.45 g | 18.65 g | 19.45 g |

TABLE 8

|  | Example 19 | Example 20 | Example 21 | Example 22 | Example 23 |
|---|---|---|---|---|---|
| Trisodium Citrate | 0.05 g | 0.05 g | 0.05 g | 0.05 g | 0.05 g |
| SAN SUPPORT ™ P-70 (Sodium Alginate) | 0.20 g | 0.20 g | 0.20 g | 0.20 g | 0.20 g |
| SAN SUPPORT ™ P-82 (Sodium Alginate) | 0.10 g | 0.10 g | 0.10 g | 0.10 g | 0.10 g |
| SAN SUPPORT ™ P-130 (Low Methoxyl Pectin) | 0.20 g | — | — | — | — |

TABLE 8-continued

|  | Example 19 | Example 20 | Example 21 | Example 22 | Example 23 |
|---|---|---|---|---|---|
| ME: 35.6% $M_w$: 67.7 kg/mol |  |  |  |  |  |
| SAN SUPPORT ™ P-140 (Low Methoxyl Pectin) ME: 10.6% $M_w$: 68.2 kg/mol | — | 0.20 g | — | — | — |
| SAN SUPPORT ™ P-150 (Low Methoxyl Pectin) ME: 5.2% $M_w$: 66.2 kg/mol | — | — | 0.20 g | — | — |
| SAN SUPPORT ™ P-160 (High Methoxyl Pectin) ME: 72.3% $M_w$: 205.2 kg/mol | — | — | — | 0.20 g | — |
| SAN SUPPORT ™ P-170 (High Methoxyl Pectin) ME: 70.6% $M_w$: 65.0 kg/mol | — | — | — | — | 0.20 g |
| Ion-exchanged Water | 19.45 g | 19.45 g | 19.45 g | 19.45 g | 19.45 g |

(3-2) Measurement Method

The viscosity before injection to simulated gastric fluid, the viscosity after, and the tube fluidity before injection to simulated gastric fluid were measured for each of the thus-prepared enteral nutritions in the same manner as in (1-2) described above.

(3-3) Results

Table 9 shows the viscosity before and after injection to simulated gastric fluid, ratio of viscosity after injection to viscosity before injection (increase in viscosity), and tube fluidity of each enteral nutrition. For comparison, Table 9 shows the test results of the enteral nutrition of Example 1 in Experiment Example 1.

TABLE 9

|  | Polysaccharide Used in Combination | Viscosity before Injection (mPa · s) | Viscosity after Injection (mPa · s) | Increase in Viscosity (Times) | Tube Fluidity (ml/hour) |
|---|---|---|---|---|---|
| Example 1 | — | 89 | 2780 | 31.2 | 788 |
| Example 15 | Alginic Add | 155 | 6250 | 40.3 | 455 |
| Example 16 | Deacylated Gellan Gum | 168 | 5900 | 35.1 | 405 |
| Example 17 | Soybean Polysaccharide | 62 | 2350 | 37.9 | 1095 |
| Example 18 | Low Methoxyl Pectin ME: 35.0%, $M_w$: 125.4 kg/mol | 165 | 5550 | 33.7 | 420 |
| Example 19 | Low Methoxyl Pectin ME: 35.6%, $M_w$: 67.7 kg/mol | 102 | 3850 | 37.7 | 670 |
| Example 20 | Low Methoxyl Pectin ME: 10.6%, $M_w$: 68.2 kg/mol | 95 | 4050 | 42.6 | 715 |
| Example 21 | Low Methoxyl Pectin ME: 5.2%, $M_w$: 66.2 kg/mol | 99 | 3980 | 40.2 | 685 |
| Example 22 | High Methoxyl Pectin ME: 72.3%, $M_w$: 205.2 kg/mol | 250 | 2040 | 8.2 | 255 |
| Example 23 | High Methoxyl Pectin ME: 70.6%, $M_w$: 65.0 kg/mol | 126 | 1820 | 14.4 | 550 |

In Example 1 and Examples 15 to 21, the viscosity before injection to simulated gastric fluid was 200 mPa·s or less, the viscosity after injection to simulated gastric fluid was 2,000 mPa·s or more, and the viscosity increased 30 times or more.

In addition, in each of these Examples, the tube fluidity was 400 ml/hour or more. Thus, the enteral nutrition of the present invention is considered to enable a care worker to help a care recipient easily take food.

In Example 15, which uses sodium alginate and alginic acid in combination, Example 16, which uses sodium alginate and deacylated gellan gum in combination, and Examples 18 to 21, which use sodium alginate and low methoxyl pectin in combination, the viscosity before injection to simulated gastric fluid was slightly higher than in Example 1; however, sufficient tube fluidity was maintained. Additionally, in Examples 18 to 21, the viscosity after injection to simulated gastric fluid increased considerably compared with that of Example 1, and the increase in viscosity was higher than in Example 1. These results reveal that combined use with alginic acid, deacylated gellan gum, or low methoxyl pectin improves the effect of increasing the viscosity of the enteral nutrition of the present invention in the stomach. In Examples 20 and 21, which use low methoxyl pectin having a methyl esterification degree ("ME") of 15% or less and a weight average molecular weight ("$M_w$") of 80,000 g/mol or less, in combination, the viscosity increased 40 times or more, and a higher effect of combined use can be observed. In Examples 22 and 23, which use high methoxyl pectin in combination, the viscosity after injection to simulated gastric fluid was lower than in Example 1, and the viscosity-increasing effect of combined use was not observed.

In contrast, in Example 17, which uses a soybean polysaccharide in combination, the viscosity before injection to simulated gastric fluid decreased, and thus, the rate of increase in viscosity from before to after injection to simulated gastric fluid was higher than in Example 1. This result reveals that the fluidity of the enteral nutrition of the present invention when injected is improved by combined use with a soybean polysaccharide.

INDUSTRIAL APPLICABILITY

The present invention provides an enteral nutrition that can be simply injected and suppress gastro-esophageal reflux.

The invention claimed is:

1. An enteral nutrition comprising 0.1 to 1.0 mass % of alginic acid and/or sodium salt thereof, calcium, and 0.1 to 3.5 parts by mass of a chelating agent per part by mass of the calcium, provided that said chelating agent is not trimagnesium phosphate;
   wherein the proportion of an alginic acid and/or a sodium salt thereof having a guluronic acid/mannuronic acid ratio (G/M ratio) of 1.5 or less is 50 to 83.3 mass % relative to the total amount of the alginic acid and/or sodium salt thereof; and
   wherein the enteral nutrition is a liquid.

2. The enteral nutrition according to claim 1, wherein tube fluidity measured by a tube fluidity measurement method is 400 ml/hour or more, wherein in the tube fluidity measurement method:
   80 ml of a sample is placed in a 100-ml plastic bottle with an opening at an upper portion;
   a flexible silicone tube with an inner diameter of 4 mm and a length of 1,000 mm is connected to the bottom of the plastic bottle;
   the bottom surface of the plastic bottle is placed 600 mm above the end of the tube so that the sample flows out only by gravity via the tube; and
   the flow A (ml) of the sample that flows out in 10 minutes is measured with a measuring cylinder, and A×6 (ml/hour) is determined to be the tube fluidity of the enteral nutrition.

3. The enteral nutrition according to claim 1, wherein a viscosity after injection to simulated gastric fluid, which is measured according to a measurement method of the viscosity after injection to simulated gastric fluid, is 1,500 mPa·s or more, wherein in the measurement method of the viscosity after injection to simulated gastric fluid:
   80 ml of a sample is placed in a 100-ml plastic bottle with an opening at an upper portion;
   a flexible silicone tube with an inner diameter of 4 mm and a length of 1,000 mm and a speed regulator are connected to the bottom of the plastic bottle;
   the flow speed is adjusted to 300 ml/hour with the speed regulator, and the total amount of the sample is directly added dropwise, via the tube, to a 100-ml beaker containing 20 ml of simulated gastric fluid (an aqueous solution containing 0.7% hydrochloric acid and 0.2% salt, pH of 1.2) maintained at 37° C. in a constant-temperature water bath; and
   the viscosity of the mixture at $1.0\ s^{-1}$ is measured by using a fluid rheometer under the following viscosity measurement conditions;
   Geometry: Cone-plate plunger with a diameter of 50 mm and a gap of 0.051 mm,
   Measurement temperature: 20° C., and
   Shear rate: $1.0\ s^{-1}$.

4. The enteral nutrition according to claim 1, wherein the proportion of an alginic acid and/or a sodium salt thereof having a weight average molecular weight (Mw) of $2.0 \times 10^5$ g/mol or less is 30 mass % or more relative to the total amount of the alginic acid and/or sodium salt thereof.

5. The enteral nutrition according to claim 1, wherein the chelating agent is citrate.

6. The enteral nutrition according to claim 1, which further comprises a polysaccharide other than alginic acid and/or sodium salt thereof.

7. The enteral nutrition according to claim 1, wherein the enteral nutrition is injected according to nasogastric or oral tube feeding, or gastrostomy or jejunostomy tube feeding.

* * * * *